United States Patent [19]

Darin et al.

[11] Patent Number: 4,895,978

[45] Date of Patent: Jan. 23, 1990

[54] OXIDATION OF PSEUDOCUMENE TO TRIMELLITIC ACID ENHANCED BY LOW GRAM ATOM RATIOS OF ZIRCONIUM TO TRANSITION METAL IN OXIDATION CATALYST SYSTEM

[75] Inventors: John K. Darin; Alan G. Bemis, both of Naperville, Ill.

[73] Assignee: Amoco Corporation, Chicago, Ill.

[21] Appl. No.: 864,813

[22] Filed: May 19, 1986

Related U.S. Application Data

[63] Continuation of Ser. No. 383,267, May 28, 1982, abandoned, which is a continuation-in-part of Ser. No. 242,551, Mar. 11, 1981, abandoned.

[51] Int. Cl.$^4$ .............................................. C07C 51/16
[52] U.S. Cl. .................................................... 562/416
[58] Field of Search ......................................... 562/416

[56] References Cited

U.S. PATENT DOCUMENTS 3,920,735  11/1975  Wampfler et al. .................. 562/416

Primary Examiner—Alan Siegel
Attorney, Agent, or Firm—James R. Henes; William H. Magidson; Ralph C. Medhurst

[57] ABSTRACT

Excess burning of pseudocumene, lowering concentration of use of cobalt and replace it with manganese by the use of less than the previously used 3.0 to 0.1 milligram atom of zirconium, preferable from 0.005 up to 0.075 milligram atom of zirconium, per 1.0 milligram atom of total of transition metals cobalt and manganese or cobalt, manganese and cerium.

3 Claims, No Drawings

OXIDATION OF PSEUDOCUMENE TO TRIMELLITIC ACID ENHANCED BY LOW GRAM ATOM RATIOS OF ZIRCONIUM TO TRANSITION METAL IN OXIDATION CATALYST SYSTEM

This is a continuation of application Ser. No. 383,267, filed May 28, 1982 now abandoned which in turn is a continuation-in-part of prior application Ser. No. 242,551 filed on Mar. 11, 1981 now abandoned.

This invention relates to the preparation of trimellitic acid by the oxidation of liquid pseudocumene (1,2,4-trimethylbenzene) with air in the presence of catalysis provided by the system: Co-Mn-Zr-Br. More particularly this invention pertains to said catalysis wherein the gram atom ratio of Zr per gram atom of the sum of Co and Mn is below 0.1:1.0.

STATE OF THE ART

According to U.S. Pat. No. 3,920,735 the systems of catalysis consisting of Mn-Br and Co-Mn-Br cause a rapid initial rate of oxygen consumption during the air oxidation of methyl groups of methylbenzenes but the oxygen consumption decreases as the methyl groups are being converted to their ultimate oxidation form, the carboxylic acid groups. Said patent further teaches that said rapid initial rate of oxygen consumption is prolonged and the activity of the systems Mn-Br, Co-Mn-Br is substantially increased by the addition of the non-transition metal zirconium to said systems of catalysis. In fact such enhancements by Zr are attained even by the unusual equi-milligram atom replacement of cobalt and/or manganese by zirconium. Another advantage coming from such use of zirconium was the decrease of intermediate oxidation products.

However, not mentioned but illustrated in U.S. Pat. No. 3,920,735 was the increase in combustion of either the methylbenzene or the reaction solvent, acetic acid when zirconium was part of the system of catalysis. Such combustion increase can be seen from a comparison of the amount (in liters) of carbon dioxide formed when zirconium is used and when it is not used.

From TABLES I, II and IV (no information in TABLE III) reporting, respectively, the oxidation of liquid oxylene, pseudocumene and p-xylene in acetic acid with air, the data following the TABLE I has been calculated.

TABLE I

| Methyl benzene | | Example | $CO_2$, Liters |
|---|---|---|---|
| O-xylene, | No Zr | A | 2.1 |
| | Zr | 1 | 4.3 |
| Pseudocumene, | No Zr | D | 5 |
| | Zr | 3 | 10.7 |
| p-xylene, | No Zr | H | 13.6 |
| | Zr | 9 | 19.4 |

U.S. Pat. No. 3,920,735 further discloses with respect to the air oxidation of pseudocumene that the results in TABLE II were not typical of commercial operation where the concentrations of components are staged rather than added all at one time as in Examples D and 3. Presented in TABLE II to follow are results from pseudocumene oxidation to trimellitic acid (TMLA) where the components of catalysis were staged and in which there were used a total of 4.87 milli-gram atoms of transition metals and 10 milligram atoms of bromine per gram mole of pseudocumene which were each about 2.2 times greater than the amounts used in said Examples D and 3.

TABLE II

| PSEUDOCUMENE OXIDATION | | | | |
|---|---|---|---|---|
| | | | Yield | |
| Zr Present | $CO_2$ Liters | Reaction Times, min. | TMLA Mole, % | Iso- and Terephthalic Acids, Mole % |
| No | 40 | 47 | 64 | 0.8 |
| Yes | 66 | 55 | 55 | 1.5 |

Such difference in commercial operation did not as drastically increase total combustion, i.e., up to 100% more $CO_2$, but it did result in a 65% increase in $CO_2$ and a 14% decrease of TMLA production.

In addition to the foregoing patent relating to a useful system of catalysis, there are also U.S. Pat. Nos. 3,354,202; 3,491,144; and 3,683,016 which pertain to modes of conduct for the oxidation of liquid pseudocumene with air in the presence of ions of bromine and one or more transition metal.

Said U.S. Pat. No. 3,354,202 is directed to the semi-continuous oxidation of polymethylbenzenes (e.g., xylenes and trimethylbenzenes) which comprises an initial batchwise oxidation initiation, a continuous mode of oxidation and a final batchwise mode of oxidation. More specifically all or part (preferably about 50%) of the solvent (e.g., acetic acid) containing components of catalysis are changed into a stirred-tank type oxidation reactor vented through a reflux condenser and a pressure reducing valve. The acetic acid solution of catalyst is heated to the oxidation initiation temperature (e.g. 170° C. to 195° C.) under a gauge pressure of 26 kg/cm² and injected with pressurized air as pseudocumene is pumped into the reaction mixture. After there is an increase in temperature of the reaction mixture the rate of introduction of air is increased by a factor of 2 to 3 to maintain a reaction temperature of from 220° to 225° C. aand at the same time (beginning of continuous mode) pseudocumene and the remainder (the other 50%) of the acetic acid with dissolved catalyst components are continuously added to the stirred reaction mixture. Injection of air at a decreasing rate is continued after all the pseudocumene and acetic acid solution have been added until the oxygen content of the exhaust gas sharply increases from about four volume percent. This concluding batchwise operation (injection of air only) is conducted to maintain a temperature of 220° C. to 225° C. by decreasing the air injection rate and, when necessary by adding heat from an external source. The catalyst components are used in weight amounts initially to provide 0.46% bromine and 0.34% cobalt and manganese on pseudocumene and 0.7 percent bromine and 0.5 percent cobalt and manganese on pseudocumene.

U.S. Pat. No. 3,491,144 is directed to the preparation of trimellitic acid by the oxidation of liquid pseudocumene with air in the presence of liquid acetic acid solution of catalyst components wherein during about the first 65 to 70 percent of the oxidation, the oxidation catalysis is provided by ions of bromine and cobalt or bromine, cerium and cobalt. Thereafter, that is for the remaining 30 to 35 percent of the oxidation, the catalysis is aided by a transition metal of e.m.f. oxidation potential lower than cobalt and cerium, preferably aided by manganese. Such oxidation of pseudocumene can be initiated at a temperature upward from 140°–145° C. and maintained at 190° to 205° C. to said 65 to 70 percent completion and then finished at a higher temperature up to 235° C. e.g., from 210° up to 235° C. The catalyst components use is not based on the pseudocumene but rather on their concentration in the acetic acid solvent. The weight ratio of acetic acid solvent to pseudocumene preferred appears to be 3.0:1.0 to 3.5:1 because such solvent ratio range is said to provide a trimellitic acid yield of about 20 mole percent increase over use of the solvent ratio range of 1.5:1 to 2:1.

On the basis of the use of a weight ratio of acetic acid to pseudocumene of 3.0:1.0 calculations using the data in Examples 1, 2, 4, and 5 of U.S. Pat. No. 3,491,144 indicates a variance with respect to the reaction's life when the addition was made and with the amount of added manganese component of catalysis. Such data with respect to components of catalysis in units of milligram atoms per 1.0 gram mole of pseudocumene are shown in TABLE III to follow.

TABLE III
STAGED ADDITION OF COMPONENTS OF CATALYSIS
Concentrations in Milligram Atoms
Per 1.0 Gram Mole Pseudocumene

| Example No. | Component | Start | Add | Mole $O_2$ | Add | Mole $O_2$ | Total |
|---|---|---|---|---|---|---|---|
| 1 | Cobalt | 4.45 | 0 | — | — | — | 4.45 |
|   | Cerium | 0.28 | 0 | — | — | — | 0.28 |
|   | Bromine | 9.45 | 0 | — | — | — | 9.45 |
|   | Manganese | 0 | 0.73 | 3.0 | — | — | 0.73 |
| 2 | Cobalt | 3.72 | 0 | — | — | — | 3.72 |
|   | Bromine | 1.96 | 0.74 | 2.5 | — | — | 2.70 |
|   | Manganese | 0 | 27.8 | 2.5 | — | — | 27.80 |
| 4 | Cobalt | 3.42 | 2.44 | 2.21 | — | — | 5.86 |
|   | Bromine | 18.0 | 13.0 | 2.21 | — | — | 31.0 |
|   | Manganese | 0 | 2.62 | 2.21 | — | — | 2.62 |
| 5 | Cobalt | 1.7 | 0.52 | 1.2 | 2.66 | 2.4 | 4.88 |
|   | Bromine | 7.8 | 8.2 | 1.2 | 15.5 | 2.4 | 31.5 |
|   | Manganese | 0 | 0 | — | 2.62 | 2.4 | 2.62 |

The stage addition of manganese, as the above data indicates, is applicable to the use of small as well as large amounts of manganese. Also said staged addition of manganese is applicable to the co-addition of small and large amounts of bromine and the co-addition of bromine and cobalt.

Lastly, U.S. Pat. No. 3,683,016 stages the addition of the transition metal (e.g., cobalt, manganese and cerium, or manganese and cerium) and bromine if desired to maintain a constant bromine-to-metal ratio. This patent teaches the use of from 0.2 to 0.4, preferably 0.28 to 0.32, weight percent total transition metals and from 1.5 to 5, preferably 1.6 to 4.5, weight percent bromine based on pseudocumene. Further with respect to the use of manganese and cerium the patent teaches that manganese should be from 10 to 25% of the total metals and cerium should be from 5 to 25%, preferably from 5 to 15%, of the total metals. Also taught is that all the cobalt component is added initially. The practice of such staged addition of catalyst components is illustrated sufficiently explicitly in Examples 1 and 3 so that the staged amounts of catalyst components can be calculated on a milligram atom per 1.0 gram mole of pseudocumene (PSC). The illustrated staged additions on that basis are shown in TABLE IV (Example 1) and TABLE V (Example 3) to follow.

TABLE IV
STAGED ADDITION OF MANGANESE, CERIUM AND BROMINE
Concentration in Milligram Atoms per 1.0 Gram Mole PSC

| Component | Start | Add | Mole $O_2$ | Total |
|---|---|---|---|---|
| Cobalt | 3.58 | 0 | — | 3.58 |
| Cerium | 0.19 | 0.26 | 4.21 | 0.45 |
| Manganese | 0.48 | 2.62 | 4.21 | 3.10 |
| Bromine | 12.0 | 1.35 | 4.21 | 13.35 |

TABLE V
STAGED ADDITION OF MANGANESE, CERIUM AND BROMINE
Concentration in Milligram Atoms per 1.0 Gram Mole PSC

| Component | Start | Add | Add | Total |
|---|---|---|---|---|
| Cobalt | 1.67 | 0 | 0 | 1.67 |
| Cerium | 0.097 | 0.214 | 0.321 | 0.632 |
| Manganese | 0.20 | 2.14 | 4.05 | 6.39 |
| Bromine | 2.625 | 5.25 | 7.875 | 15.75 |

For more complete details of the mode of operation of the processes of the four foregoing patents, each of their complete disclosures, descriptions and examples are incorporated herein by the foregoing reference to each patent by its specific number.

The foregoing U.S. patents are, as far as we know, the closest of the state of the art to the present invention. The essential features of the oxidation method of said patents are the use of 2 to 5 milligram atoms of the transition metal manganese or total of manganese and cobalt with 2 to 10 milligram atoms of bromine and from 1.0 up to 2.0 milligrams atoms of zirconium per one gram mole of pseudoceumene transition metal. The milligram atom ratio of Zr to total transition metal this is in the range of 0.2:1.0 to 1.0:1.0.

BENEFITS OF THE PRESENT INVENTION

To decrease the total combustion of methylbenzene and/or acetic acid reaction solvent by decreasing zirconium use by the present invention occurs without a corresponding increase in the production of oxidation intermediates and/or co-products, especially iso- and terephthalic acids. We have demonstrated that iso- and terephthalic acids appearing in the trimellitic acid result from the destruction of the methyl-substituent in the 1- and/or the 2-positions of pseudocumene. Destruction of the 1-methyl group leads to isophthalic acid by the expected oxidation of the 2- and 4-position methyl groups to carboxylic acid groups. Likewise destruction of the 2-methyl group leads to terephthalic acid by the expected oxidation of the 1- and 4-positioned methyl groups to carboxylic acid groups. Although destruction of said methyl groups does occur, the disappearance of the methyl groups and their replacement by hydrogen in an oxidation environment is not understood. Previously the appearance of iso- and terephthalic acid in the terephthalic acid was attributed to m- and p-xylene contamination of pseudocumene. However, as its m- and p-xylene contamination were decreased the iso- and terephthalic acid content of trimellitic acid product was not similarly decreased.

Practice according to the present invention involves the use of very low concentrations of zirconium to promote the activity of the transition metals, the decrease of the concentration of cobalt used, and the replacement of the cobalt with manganese and not with zirconium as taught in U.S. Pat. No. 3,920,735. It is surprising that said departures from the practice according to said practice results in retaining the high trimellitic acid yields, decreases reaction time by even further enhancing catalytic activity, and by decreasing total combustion. Further, it is surprising that the very low zirconium concentrations used according to the practice of this invention permits the use of manganese of up to 60% of the total initially charged metals without incurring the sluggish incomplete reactions as forecast by U.S. Pat. No. 3,491,144. In addition it is surprising that the present low concentration use of zirconium provides the option of omitting the use of cerium. Lastly, it is also surprising that the present low concentration use of zirconium substantially overcomes the oxidation inhibiting effect of corrosion metals, especially iron. These and other advantages and benefits of the present invention will become apparent to those skilled in the art from the following detailed description of the present invention and the illustrated modes of its practice.

STATEMENT OF THE INVENTION

The present invention is for the oxidation of liquid pseudocumene with air in the presence of liquid acetic acid as reaction solvent at a temperature in the range of from 175° C. up to 225° C. in the presence of a system of catalysis based on one (1.0) gram mole of pseudocumene of the ions comprising the transition metals, an amount of from 2.5 up to 5.5 milligram atoms total of cobalt and manganese, and cerium if present, and by from 2.25 up to 5. milligram atoms of bromine modified by from only 0.005 up to 0.075 milligram atoms of zirconium per 1.0 milligram atom of the total of transition metals. Preferably there are used for each 1.0 gram mole of pseudocumene from 2.95 up to 3.75 total milligram atoms of cobalt and manganese, from 2.4 up to 3.3 milligram atoms of bromine and for each 1.0 milligram atom of cobalt and manganese from 0.005 up to 0.05 milligram atoms of zirconium. In said preferred range of total cobalt and manganese transition metals it is preferred that the manganese comprise from 24% up to 60% of the transition metal total.

The reaction temperature of 175° to 225° C. is conventional in the art of preparation of trimellitic acid by the oxidation of liquid pseudocumene (1,2,4-trimethylbenzene) with air in the presence of catalysis provided by a combination of ions of bromine and one or more transition metals, especially manganese and cobalt or manganese, cobalt and cerium.

The reaction solvent is acetic acid which since 1960 has become the solvent of choice from the $C_2$ to $C_8$ monocarboxylic acids which include the aliphtic, alicyclic and aromatic (benzoic) acids. The amount of reaction solvent relative to pseudocumene being oxidized has preferably (from U.S. Pat. No. 3,491,144) been in the weight ratio of acetic acid to pseudocumene of from 3.0:1.0 to 3.5 to 1.0 because lower weight ratios of 1.5:1.0 to 2:1 were disclosed as decreasing the yield of desired trimellitic acid by about 20 mole percent. However, the benefits of the present invention can be obtained, surprisingly, by the use of an acetic acid to pseudocumene weight ratio as low as about 0.6:1.0. But, if desired, the higher ratios up to 3.6:1.0 can still be used without loss of the benefits of the present invention.

The oxidation of liquid pseudocumene with air in the presence of liquid acetic acid can be carried out at a temperature within the range of from 160° C. up to 225° C. For example, as the previously discussed state of the art discloses, the oxidation can be initiated at a temperature of 160° C., be permitted to be conducted at a higher temperature of 185° to 195° C. and then be completed at a temperature of 205° to 225° C. Since acetic acid and pseudocumene boil at temperatures below 160° C., the oxidation process of this invention is carried out at the super atmospheric pressure required to maintain acetic acid and pseudocumene in the liquid phase. For such 175° to 225° C. reaction temperatures reaction pressures of from 22 up to 30 kg/cm² gauge pressure are adequate to maintain such liquid phase conditions.

The following two commercial oxidations of pseudocumene: one by the practice prior to this invention (Comparative Example I) and the other by the practice according to U.S. Pat. No. 3,920,735 (Comparative Example II) will illustrate benefits to be attained by the latter prior practice. Both oxidations were conducted under the same conditions except for the components of catalysis. That is, the oxidations were started by setting the reaction pressure at 29.5 kg/cm² gauge; adding acetic acid to provide a weight ratio thereof total pseudocumene to be added of 1.85:1.0 and 100% of the pseudocumene and the initial mounts of components of catalysis to a stirred reaction vessel. Its contents were heated to initiation reaction temperature of 106° C. and then injected with pressurized air until the temperature of the reaction mixture increased. Thereafter the rate of injection of pressurized air was increased to maintain a reaction temperature between 185° and 195° C. during this continuous phase of injection of air. An acetic acid solution of the second amount of components of catalysis was added, the reaction temperature was increased to 205°–225° C. where it was maintained even with the application of externally applied heat when necessary and the injection of pressurized air was gradually decreased to maintain the exhaust gas' oxygen content at less than 8 volume percent. Then, upon a sudden increase in said oxygen content to 16 volume percent, indicating no further oxidation was taking place, the injection of air was stopped and the reaction mixture was discharged for recovery of trimellitic acid.

The composition of the initial system of catalysis and the added composition are given in TABLE VI to follow in milligram atoms (mga) of each component per 1.0 gram mole of pseudocumene (PSC) charged. The by- and coproducts of the oxidation are given in mole percent of pseudocumene charged.

TABLE VI

| OXIDATION OF LIQUID PSEUDOCUMENE WITH AIR | | | | |
|---|---|---|---|---|
| | Comparative Example I Concentration mga | | Comparative Example II Concentration mga | |
| Components of Catalysis | Initial | Added | Initial | Added |
| Bromine | 4.8 | 0 | 4.8 | 0 |
| Cobalt | 3.8544 | 0 | 3.05 | 0 |
| Manganese | 0 | 1.7454 | 0.61 | 0.44 |
| Cerium | 0.197 | 0.077 | 0.197 | 0.077 |
| Zirconium | 0 | 0 | 0.0224 | 0.53 |
| Reaction Time | 85 minutes | | 82 minutes | |
| Zr/Transition Metals | — | | 0.125:1.0 | |
| Final O₂ in Exhaust | 16 vol. % | | 16 vol. % | |
| Yields, Mole % | | | | |
| o-phthalic acid | 0.87 | | 0.89 | |
| Total IPA and TPA* | 1.25 | | 1.20 | |
| Methyl/Phthalic Acids | 0.30 | | 0.05 | |

*IPA and TPA mean iso- and terephthalic acids

The above batchwise oxidation of liquid pseudocumene are repeated with slightly different catalyst component concentrations. Said conditions, reaction time, final exhaust oxygen content and mole % yields are shown in TABLE VII to follow.

TABLE VII

PSC OXIDATIONS WITH AIR WITH LOW OR NO ZIRCONIUM

| Components of Catalysis | Comparative Example III Concentration mga | | Example 1 Concentration mga | |
|---|---|---|---|---|
| | Initial | Added | Initial | Added |
| Bromine | 5.1 | 0 | 5.1 | 0 |
| Cobalt | 4.06 | 0 | 2.85 | 0 |
| Manganese | 0 | 1.75 | 0 | 1.27 |
| Cerium | 0.43 | 0.086 | 0.43 | 0.086 |
| Zirconium | 0 | 0 | 0.0263 | 0.086 |
| Zr/Transition Metals | — | | 0.0057:1.0 | |
| Reaction Time | 85 minutes | | 74 minutes | |
| Final O₂ in Exhaust | 18 vol. % | | 18 vol. % | |
| Yields, Mole % | | | | |
| o-phthalic acid | 0.9 | | 0.9 | |
| Total IPA and TPA* | 1.5 | | 1.2 | |
| Methyl/Phthalic Acids | 0.7 | | 0.16 | |
| Trimellitic Acid | 73 | | 81 | |
| PSC Burned | 7.1 | | 6.1 | |

*IPA and TPA mean iso- and terephthalic acids

As the comparison in TABLE II between no zirconium and the use of zirconium show, the high concentration of zirconium (1.85 milligram atoms per 1.0 gram mole of PSC) decrease the yield of desired trimellitic acid from that when no zirconium was used. However, the data in TABLE VII show the the use of only 1/70 as such (1.85 divided by 0.0263) zirconium provides a 1.0 mole percent decrease in PSC burning, a decrease in both IPA and TPA products, a decrease in methylphthalic acids products while providing about eleven percent increase in trimellitic acid production over no zirconium use.

In Table VIII to follow there are shown the results from two further oxidations similar to Example 1 above but using one half the bromine, no cerium, less cobalt and more manganese. The initial manganese in Example 2 is 18.7% of the total transition metals. The manganese concentration in the initial catalyst of Example 3 is 48% of the metals which U.S. Pat. No. 3,683,016 would forecast as causing a rather slow and incomplete reaction. However as the data of Example 3 show the same was not so but rather the reaction was more complete and did provide a higher yield of trimellitic acid.

TABLE VIII

ELIMINATION OF CERIUM, LOWERING COBALT AND ZIRCONIUM, AND INCREASING MANGANESE CONCENTRATIONS

| Catalyst Component | Example 2 | | Example 3 | |
|---|---|---|---|---|
| | Initial mga | Added mga | Initial mga | Added mga |
| Bromine | 2.4 | 0 | 2.4 | 0 |
| Cobalt | 2.85 | 0 | 1.63 | 0 |
| Manganese | 0.655 | 0.218 | 1.53 | 0.436 |
| Zirconium | 0.053 | 0.066 | 0.132 | 0.066 |
| Zr:Transition metals | 0.032:1.0 | | 0.055:1.0 | |
| Reaction Time | 77 minutes | | 80 minutes | |
| Final O₂ | 16 vol. % | | 16 vol. % | |
| Yields, Mole % | | | | |
| o-phthalic acid | 0.86 | | 0.91 | |
| Total IPA and TPA* | 1.21 | | 1.18 | |
| Methyl/Phthalic Acids | 0.15 | | 0.20 | |
| Trimellitic Acid | 82.3 | | 84.2 | |

TABLE VIII-continued

ELIMINATION OF CERIUM, LOWERING COBALT AND ZIRCONIUM, AND INCREASING MANGANESE CONCENTRATIONS

| Catalyst Component | Example 2 | | Example 3 | |
|---|---|---|---|---|
| | Initial mga | Added mga | Initial mga | Added mga |
| PSC Burned | 6.2 | | 6.0 | |

*IPA and TPA mean iso- and terephthalic acids.

Further illustrations of the practice of the present invention are shown by Examples 4, 5, and 6 whose operating and results data are shown in TABLE IX to follow. In Example 4 (as in Example 2 above) the low zirconium with prior high cobalt is presented for comparison with the lower cobalt, low zirconium and higher manganese of Examples 5 and 6. Example 6 shows a slight increase in intermediate products, a 21 mole % increase (from 6.0 to 7.3 mole %) in PSC burning and a decrease in trimellitic acid produced and hence is at about the lower limit of cobalt decrease for which increases in manganese and zirconium cannot compensate.

TABLE IX

APPROACHING LIMITS OF DECREASE OF COBALT CONCENTRATING
Catalyst Components in Milligram Atoms Per 1.0 Gram Mole PSC

| Catalyst Component | Example 4 | | Example 5 | |
|---|---|---|---|---|
| | Initial mga | Added mga | Initial mga | Added mga |
| Bromine | 3.3 | 0 | 3.3 | 0 |
| Cobalt | 2.85 | 0 | 2.03 | 0 |
| Manganese | 0.654 | 0.218 | 1.09 | 0.218 |
| Zirconium | 0.053 | 0.066 | 0.105 | 0.066 |
| Zr/Transition Metal | 0.033:1.0 | | 0.05:1.0 | |
| Reaction Time | 71 minutes | | 73 minutes | |
| Final O₂ in Exhaust | 18 vol. % | | 18 vol. % | |
| Yields, Mole % | | | | |
| o-phthalic acid | 0.90 | | 0.86 | |
| Total IPA and TPA* | 1.16 | | 1.15 | |
| Methyl/Phthalic Acids | 0.38 | | 0.35 | |
| Trimellitic Acid | 80.4 | | 80.1 | |
| PSC Burned | 6.0 | | 5.9 | |

| Catalyst Component | Example 6 | |
|---|---|---|
| | Initial mga | Added mga |
| Bromine | 3.3 | 0 |
| Cobalt | 1.22 | 0 |
| Manganese | 1.53 | 0.218 |
| Zirconium | 0.158 | 0.218 |
| Zr/Transition Metals | 0.075:1.0 | |
| Reaction Time | 78 minutes | |
| Final O₂ in Exhaust | 18 vol. % | |
| Yields, Mole % | | |
| o-phthalic acid | 1.05 | |
| Total IPA and TPA* | 1.16 | |
| Methyl/Phthalic Acids | 0.31 | |
| Trimellitic Acid | 79.3 | |
| PSC Burned | 7.3 | |

*IPA and TPA mean iso- and terephthalic acids

Iron contamination begins to be a significant oxidation inhibitor at an iron to cobalt gram atom ratio of 1:100. By the use of zirconium as a component of catalysis the adverse effect of iron is surprisingly substantially overcome. Such effect of zirconium is illustrated in TABLE X to follow wherein oxidations of PSC are contaminated with massive amount of corrosion metals iron, nickel and chromium known to inhibit oxidation of methylbenzenes. For comparative purposes there is presented an iron, nickel and chromium contaminated PSC oxidation without zirconium. Except for the catalyst composition differences and differences in corrosion metals, the two oxidations were identically conducted.

TABLE X

ZIRCONIUM SUPPRESSION OF INHIBITION BY CORROSION METALS
Catalyst Components and Contaminants
Concentration in mga per 1.0 gram Mole of PSC

| Catalyst Components | Example 7 | Comparative Example IV |
|---|---|---|
| Cobalt | 2.85 | 2.85 |
| Manganese | 1.09 | 1.31 |
| Cerium | 0.206 | 0.206 |
| Zirconium | 0.132 | 0 |
| Bromine | 5.1 | 5.1 |
| Zr/Transition Metals | 0.032:1.0 | — |
| Corrosion Metals: | | |
| Iron | 5.14 | 2.14 |
| Chromium | 0.69 | 0.23 |
| Nickel | 0.082 | 0.041 |
| Fe:Co | 180:100 | 75:100 |
| Molar Yields, %: | | |
| o-Phthalic Acid | 0.84 | 0.68 |
| Total IPA and TPA* | 1.06 | 0.96 |
| Methyl/Phthalic Acids | 0.39 | 10.0 |
| Trimellitic Acid | 77.7 | 43.1 |
| PSC Burned, mole % | 6.2 | 4.7 |
| Reaction Time, min. | 78 | 75 |
| Final $O_2$ in Exhaust | 18 vol. % | 18 vol. % |

*IPA and TPA mean iso- and terephthalic acids.

Finally, to conduct, by what we presently believe to be the optimum, including the best mode of operation, the present invention to obtain the optimum results there are presented Examples 8, 9, and 10. The operating and resulting data for those Examples are shown in TABLE XI to follow. Comparative Example V, conducted by the before described manner, uses a zirconium to total transition metals milligram atom ratio of 0.111:1.0 which is substantially the same as the lowest ratio contemplated by the patentees of U.S. Pat. No. 3,920,735 for the oxidation of m- and p-xylene but only about one half the lowest ratio the patentees contemplated for the oxidation of pseudocumene. But as the data show, said ratio of 0.111:1.0 of Zr to total transition metals did not decrease the total combusting of pseudocumene nor did it increase the yield of trimellitic acid.

TABLE XI

LOW ZIRCONIUM PROMOTION OF COBALT-MANGANESE-BROMINE SYSTEM OF CATALYSIS FOR PSC OXIDATION
All Catalyst Components Concentration mga per gram mole PSC

| Catalysis Component | Example 8 Initial mga | Example 8 Added mga | Example 9 Initial mga | Example 9 Added mga |
|---|---|---|---|---|
| Bromine | 2.4 | 0 | 2.4 | 0 |
| Cobalt | 1.63 | 0 | 1.63 | 0 |
| Manganese | 1.53 | 0.218 | 1.53 | 0.436 |
| Zirconium | 0.158 | 0.066 | 0.132 | 0.132 |
| Zr/Transition Metal | 0.066:1.0 | | 0.073:1.0 | |
| Reaction Time | 80 minutes | | 80 minutes | |
| Final $O_2$ in Exhaust | 18 vol. % | | 18 vol. % | |
| Molar Yields, % | | | | |
| o-phthalic acid | 0.90 | | 0.92 | |
| Total IPA and TPA* | 1.11 | | 1.17 | |
| Methyl/Phthalic Acids | 0.39 | | 0.39 | |
| Trimellitic Acid | 81.9 | | 83.0 | |
| PSC Burned, mole % | 6.5 | | 6.7 | |

| Catalysis Component | Example 10 Initial mga | Example 10 Added mga | Comparative V Initial mga | Comparative V Added mga |
|---|---|---|---|---|
| Bromine | 2.4 | 0 | 3.96 | 0 |
| Cerium | 0 | 0 | 0.18 | 0 |
| Cobalt | 1.63 | 0 | 3.25 | 0 |
| Manganese | 1.53 | 0.436 | 0 | 1.31 |
| Zirconium | 0.132 | 0.066 | .5275 | 0 |
| Zr/Transition Metals | 0.055:1.0 | | 0.111:1.0 | |
| Reaction Time | 80 minutes | | 65 minutes | |
| Final $O_2$ in Exhaust | 18 vol. % | | 18 vol. % | |
| Yields, Mole % | | | | |
| o-phthalic acid | 0.91 | | 0.91 | |
| Total IPA and TPA* | 1.18 | | 1.33 | |
| Methyl/Phthalic Acids | 0.39 | | 0.14 | |
| Trimellitic Acid | 84.2 | | 70 | |
| PSC Burned, mole % | 6. | | 9.4 | |

*IPA and TPA mean iso- and terephthalic acids

The invention claimed is:

1. The method of oxidation of liquid pseudocumene in the presence of acetic acid in the weight ratio to pseudocumene of from 0.6:1.0 up to 3.5:1.0 at a temperature of from 175° C. up to 225° C. in the presence of a system of catalysis based on one gram mole of pseudocumene of from 2.25 up to 5.1 milligram atoms of bromine, a total of from 2.5 up to 5.5 milligram atoms of transition metals cobalt, manganese and cerium and from 0.005 up to 0.075 milligram atoms of zirconium per milligram atom of total transition metal.

2. The oxidation method of claim 1 wherein for each one gram mole of pseudocumene there is a total of from about 2.95 up to 3.75 total milligram atoms of cobalt and manganese as transition metal, from 2.4 up to 3.3 milligram atom of bromine and for each 1.0 milligram atoms of total transition metal from 0.0005 up to 0.05 milligram atoms of zirconium.

3. The method of claim 2 where in the manganese comprises from 24% up to 60% of the total of cobalt and manganese portion of the catalyst system.

* * * * *